United States Patent
Howard et al.

(10) Patent No.: US 6,511,827 B1
(45) Date of Patent: Jan. 28, 2003

(54) NUCLEOTIDE ENCODING HUMAN GALANIN RECEPTOR 3 (GALR3)

(75) Inventors: Andrew D. Howard, Park Ridge, NJ (US); Margaret A. Cascieri, East Windsor, NJ (US); Roy G. Smith, Houston, TX (US); Kathleen A. Sullivan, Springfield, NJ (US); Carina Tan, Metuchen, NJ (US); Leonardus H. T. Van Der Ploeg, Scotch Plains, NJ (US); Kevin R. Lynch, Charlottesville, VA (US)

(73) Assignee: Merck & Co., Inc., Rahway, NJ (US)

( * ) Notice: Subject to any disclaimer, the term of this patent is extended or adjusted under 35 U.S.C. 154(b) by 28 days.

(21) Appl. No.: 09/595,549

(22) Filed: Jun. 16, 2000

Related U.S. Application Data

(63) Continuation of application No. PCT/US98/26812, filed on Dec. 17, 1998.
(60) Provisional application No. 60/069,725, filed on Dec. 17, 1997, now abandoned.

(51) Int. Cl.$^7$ .................. C12N 15/12; C12N 15/63; C12N 5/10
(52) U.S. Cl. .................. 435/69.1; 435/320.1; 435/325; 536/23.5
(58) Field of Search .................. 536/23.5; 435/325, 435/320.1, 69.1

(56) References Cited

FOREIGN PATENT DOCUMENTS

| EP | 0711830 A2 | 5/1996 |
| WO | WO 92/15681 | 9/1992 |
| WO | WO 97/26853 | 7/1997 |
| WO | WO 97/46681 | 12/1997 |
| WO | WO 98/03548 | 1/1998 |
| WO | WO 08/15570 | * 4/1998 |

OTHER PUBLICATIONS

Habert–Ortoli, E. et al.; Molecular Cloning of a Functional Human Galanin Receptor; Proc. Natl. Acad. Sci. USA; vol. 91; pp. 9780–9783; 1994.

Sequence comparison to Gen–Bank Accession No. Z82241, Jan. 13, 1997.

Gen–Bank Accession No. Z97630, Oct. 29, 1997.

* cited by examiner

Primary Examiner—Michael Pak
(74) Attorney, Agent, or Firm—Joanne M. Giesser; Alysia A. Finnegan

(57) ABSTRACT

A new galanin receptor, GALR3, is described. Also provided are nucleic acids encoding same and various assays to identify ligands particular to said receptor. Ligands so identified are useful for the treatment of obesity, treatment of pain, and treatment of cognitive disorders.

8 Claims, 12 Drawing Sheets ccaggtcgggggagttagatcccgggggtcaagcaaccagaactgggggctcttgcctgaggattcc
agcttctcttcccaggtgcccgtctgatggggagATGGCTGATGCCCAGAACATTTC
ACTGGACAGCCCAGGGAGTGTGGGGGCCGTGGCAGTGCCTGTG
GTCTTTGCCCTAATCTTCCTGCTGGGCACAGTGGGCAATGGGCTG
GTGCTGGCAGTGCTCCTGCAGCCTGGCCCGAGTGCCTGGCAGGA
GCCTCGCAGCACCACGGACCTGTTCATCCTCAACCTGGCGGTGG
CTGACCTCTGCTTCATCCTGTGCTGCGTGCCCTTCCAGGCCACCAT
ATACACGCTGGATGCCTGGCTCTTTGGGGCCCTCGTTTGCAAGGC
CGTGCACCTGTTCATCTACCTCACCATGAACGCCAGCAGCTTTAC
GCTGGCTGCTGTATCTGTGGACAGgtgcgctgtgcctggggcctggtgggcagg
gctgtgggggcgggggttggggaggagtcctgaacagatcctcactggccttaggaaggagaga
gtgggggaccagaaagggaggtgggtgggaggaaacaaaagctccctgaccccctcgcaagcgc
ctctgggcacctgcagggcgtgcttgaggggactgtcctgcccttcccctcctccactgtgaacttccag
aggacgcctctgagtctcaagtggcagcacagggtctggcacatagtaagtgctctgtaagcgcgaa
atgaatcgcaaaagaagctcacgaatgcgttcatcagttttttttgttttgttttgttttgttgttttttttttttgg
atcttggctcactgcaacctctgcctcctgggttccagcgattctcctgccacagcctcctgagtagctgg
gattacaggccaccacacctggctaattttttgtattttagtagaaacggggttttgccatgttggacag
gctggtctcgaaccccctgacctcaagtgatccgcccgcctcggcctcccaagtgctgggattacaggc
gtgagccaccgcgcccagcccagctatttttctaactgcccacacctggccaagctgtgcacacatctg
cttccacagcttgaaacttggggtcaaatccaggctcactccagctgatgaccctgggcaagtcacttc
tctctggacctcatctgacgcatccataaaataatcctagaaataacaagtcaccgggatcgggcccctt
gctaggtgcaagggcctaagcaccttgcgcgttcacacccttaatccccgccacgtcccccacggttc
acaggaggcgcactgggccgcagggcccggcgcgggacgtggcgcgggcccctgcgggaggg
cacctgcccgccccgctgaccasgcgccctccgcagGTACCTGGCCGTGCGGCACC
CGCTGCGCTCGCGCGCCCTGCGCACGCCGCGTAACGCCCGCGCC
GCAGTGGGGCTGGTGTGGCTGCTGGCGGCGCTCTTCTCGGCGCC
CTACCTCAGCTACTACGGCACCGTGCGCTACGGCGCGCTGGAGC
TCTGCGTGCCCGCCTGGGAGGACGCGCGCCGCCGCGCCCTGGAC
GTGGCCACCTTCGCTGCCGGCTACCTGCTGCCCGTGGCYGTGGTG
AGCCTGGCCTACGGGCGCACGCTGCGCTTCCTGTGGGCCGCCGT
GGGTCCCGCGGGCGCGGCGGCRGCCAAGGCGCGGCGGAGGGCG
ACKGGCCGCGCGGGGCGCGCCATGCTGGCGGTGGCCGCGCTCTA
CGCGCTMTGCTGGGGTCCGCACCACGCGCTCATCCTGTGCTTCTG
GTACGGCCGMTTCGCCTTCAGCCCGGCCACCTACGCMTGCCGCC
TGGCCTCACACTGCCTGGCCTACGCCAACTCMTGCCTCAACCCGC
TCGTMTACGCGCTCGCCTCGCGCCACTTCCGCGCGCGCTTCCGCC
GCCTGTGGCCGTGCGGYCGCCGACGCCGCCACCGTGCCCGCCGC
GCCTTGCGTCGCGTCCGCCCCGCGTCCTCGGGCCCACCCGGCTGC
CCCGGAGACGCCCGGCCTAGCGGGACGCTGCTGGCTGGTGGCGG
CCAGGGCCCSGAGCCCAGGGAGGGACCCGTCCACGGCGGAGAG
GCTGCCCGAGGACCGGAATAAaccctgccgcctggactccgcctgtgtccgtctgtct
cactcccgttctccgaaggcgggacgccaccgggccagggatggggcaatgccacgagctc

FIG.1

With Standard Genetic Code

Molecular Weight 39600.44 Daltons
   368 Amino Acids
   41 Strongly Basic(+) Amino Acids (K,R)
   16 Strongly Acidic(-) Amino Acids (D,E)
   173 Hydrophobic Amino Acids (A,I,L,F,W,V)
   71 Polar Amino Acids (N,C,Q,S,T,Y)

10.463 Isolectric Point
   25.882 Charge at PH 7.0

Total number of bases translated is 1107
   % A = 10.66 [118]
   % G = 33.42 [370]
   % T = 17.34 [192]
   % C = 37.58 [416]

% Ambiguous = 0.99    [11]

% A+T = 28.00 [310]
   % C+G = 71.00 [786]

Davis,Botstein,Roth Melting Temp C. 93.56
   Wallace Temp C       4618.00

Codon usage:
```
gca Ala(A)  3 # cag Gln(Q) 5 # uug Leu(L)  1 # uaa Ter(.)  1
gcc Ala(A) 33 # --- Gln(Q) 5 # --- Leu(L) 48 # uag Ter(.)  0
gcg Ala(A) 19 # gaa Glu(E) 1 # aaa Lys(K)  0 # uga Ter(.)  0
gcu Ala(A)  7 # gag Glu(E) 6 # aag Lys(K)  1 # --- Ter(.)  1
--- Ala(A) 62 # --- Glu(E) 7 # --- Lys(K)  1 # ace Thr(T)  1
aga Arg(R)  0 # gga Gly(G) 4 # aug Met(M)  3 # acc Thr(T)  6
agg Arg(R)  3 # ggc Gly(G)15 # --- Met(M)  3 # acg Thr(T)  6
cga Arg(R)  2 # gag Gly(G) 8 # uuc Phe(F) 13 # ecu Thr(T)  0
cgc Arg(R) 26 # ggu Gly(G) 3 # uuu Phe(F)  3 # --- Thr(T) 13
cgg Arg(R)  4 # --- Gly(G)30 # --- Phe(F) 16 # ugg Trp(W)  8
cgu Arg(R)  3 # cac His(H) 8 # cca Pro(P)  2 # --- Trp(W)  8
--- Arg(R) 38 # cau His(H) 0 # ccc Pro(P) 10 # uac Tyr(Y) 14
aac Asn(N)  6 # --- His(H) 8 # ccg Pro(P)  8 # uau Tyr(Y)  0
aau Asn(N)  1 # aua He(I)  1 # ccu Pro(P)  4 # --- Tyr(Y) 14
--- Asn(N)  7 # auc He(I)  5 # --- Pro(P) 24 # gua Val(V)  1
gac Asp(D)  7 # auu Be(I)  1 # agc Ser(S)  8 # guc Val(V)  3
gau Asp(D)  2 # --- Be(I)  7 # agu Ser(S)  2 # gug Val(V) 22
--- Asp(D)  9 # cue Leu(L) 1 # uca Ser(S)  2 # guu Val(V)  1
ugc Cys(C) 12 # cuc Leu(L)14 # ucc Ser(S)  1 # --- Val(V) 27
ugu Cys(C)  0 #cug Leu(L) 32 #ucg Ser(S)   4 #nnn ???(X)  11
--- Cys(C) 12 # cuu Leu(L) 0 # ucu Ser(S)  1 #TOTAL 369
caa Gln(Q)  0 # uua Leu(L) 0 # --- Ser(S) 18 #
```

FIG.2A

MADAQNISLDSPGSVGAVAVPVVFALIFLLGTVGNGLVLAVLLQPG
PSAWQEPRSTTDLFILNLAVADLCFILCCVPFQATIYTLDAWLFGAL
VCKAVHLFIYLTMNASSFTLAAVSVDRYLAVRHPLRSRALRTPRNA
RAAVGLVWLLAALFSAPYLSYYGTVRYGALELCVPAWEDARRRAL
DVATFAAGYLLPVAVVSLAYGRTLRFLWAAVGPAGAAAAKARRR
ATGRAGRAMLAVAALYALCWGPHHALILCFWYGRFAFSPATYAC
RLASHCLAYANSCLNPLVYALASRHFRARFRRLWPCGRRRRHRAR
RALRRVRPASSGPPGCPGDARPSGTLLAGGGQGPEPREGPVHGGEA
ARGPE

FIG.2B

```
ATGGCTGATGCCCAGAACATTTCACTGGACAGCCCAGGGAGTGT
GGGGGCCGTGGGAGTGCCTGTGGTCTTTGCCCTAATCTTCCTGCT
GGGCACAGTGGGCAATGGGCTGGTGCTGGCAGTGCTCCTGCAGC
CTGGCCCGAGTGCCTGGCAGGAGCCTGGCAGCACCACGGACCTG
TTCATCCTCAACCTGGCGGTGGCTGACCTCTGCTTCATCCTGTGCT
GCGTGCCCTTCCAGGCCACCATCTACACGCTGGATGCCTGGCTCT
TTGGGGCCCTCGTCTGCAAGGCCGTGCACCTGCTCATCTACCTCA
CCATGTACGCCAGCAGCTTTACGCTGGCTGCTGTCTCCGTGGACA
GGTACCTGGCCGTGCGGCACCCGCTGCGCTCGCGCGCCCTGCGC
ACGCCGCGTAACGCCCGCGCCGCAGTGGGGCTGGTGTGGCTGCT
GGCGGCGCTCTTCTCGGCGCCCTACCTCAGCTACTACGGCACCGT
GCGCTACGGCGCGCTGGAGCTCTGCGTGCCCGCCTGGGAGGACG
CGCGCCGCCGCGCCCTGGACGTGGCCACCTTCGCTGCCGGCTAC
CTGCTGCCCGTGGCTGTGGTGAGCCTGGCCTACGGGCGCACGCT
GCGCTTCCTGTGGGCCGCCGTGGGTCCCGCGGGCGCGGCGGCGG
CCGAGGCGCGGCGGAGGGCGACGGGCCGCGCGGGGCGCGCCAT
GCTGGCGGTGGCCGCGCTCTACGCGCTCTGCTGGGGTCCGCACC
ACGCGCTCATCCTGTGCTTCTGGTACGGCCGCTTCGCCTTCAGCC
CGGCCACCTACGCCTGCCGCCTGGCCTCACACTGCCTGGCCTACG
CCAACTCCTGCCTCAACCCGCTCGTCTACGCGCTCGCCTCGCGCC
ACTTCCGCGCGCGCTTCCGCCGCCTGTGGCCGTGCGGCCGCCGAC
GCCGCCACCGTGCCCGCCGCGCCTTGCGTCGCGTCCGCCCCGCGT
CCTCGGGCCCACCCGGCTGCCCCGGAGACGCCCGGCCTAGCGGG
AGGCTGCTGGCTGGTGGCGGCCAGGGCCCGGAGCCCAGGGAGG
GACCCGTCCACGGCGGAGAGGCTGCCCGAGGACCGGAATAA
```

FIG.3

MADAQNISLDSPGSVGAVAVPVVFALIFLLGTVGNGLVLAVLLQPG
PSAWQEPGSTTDLFILNLAVADLCFILCCVPFQATIYTLDAWLFGAL
VCKAVHLLIYLTMYASSFTLAAVSVDRYLAVRHPLRSRALRTPRNA
RAAVGLVWLLAALFSAPYLSYYGTVRYGALELCVPAWEDARRRAL
DVATFAAGYLLPVAWSLAYGRTLRFLWAAVGPAGAAAAEARRR
ATGRAGRAMLAVAALYALCWGPHHALILCFWYGRFAFSPATYAC
RLASHCLAYANSCLNPLVYALASRHFRARFRRLWPCGRRRRHRAR
RALRRVRPASSGPPGCPGDARPSGRLLAGGGQGPEPREGPVHGGEA
ARGPE

FIG.4

```
mGALR1    1  MELAMVNLSEGNGSDPEPPAPESRPLFGIGVEN  33
rGALR1    1  MELAPVNLSEGNGSDPEPPA-EPRPLFGIGVEN  32
hGALR1    1  MELAVGNLSEGNASCPEPPAPEPGPLFGIGVEN  33
hGALR3.2  1  M-----A--DAQNISLDSP--GSV---G----A  17
hGALR3.3  1  M-----A--DAQNISLDSP--GSV---G----A  17
rGALR3    1  ---------------------------------   0
mGALR2    1  M-----NGSDSQGAEDSSQEGG-G---GWQPEA  24
rGALR2    1  M-----NGSGSQGAENTSQEGGSG---GWQPEA  25
hGALR2    1  M-----NVSGCPGAGNASQAGGGG---GWHPEA  25 mGALR1   34  FITLVVFGLIFAMGVLGNSLVITVLARSKPGK-  65
rGALR1   33  FITLVVFGLIFAMGVLGNSLVITVLARSKPGK-  64
hGALR1   34  FVTLVVFGLIFALGVLGNSLVITVLARSKPGK-  65
hGALR3.2 18  VAVPVVFALIFLLGTVGNGLVLAVLLQPGPSAW  50
hGALR3.3 18  VAVPVVFALIFLLGTVGNGLVLAVLLQPGPSAW  50
rGALR3    1  ---------------------------------   0
mGALR2   25  VLVPLFFALIFLVGAVGNALVLAVLLRGG      53
rGALR2   26  VLVPLFFALIFLVGAVGNALVLAVLLRGG      54
hGALR2   26  VIVPLLFALIFLVGTVGNTLVLAVLLRGG      54 mGALR1   66  --PRSTTNLFILNLSIADLAYLLFCIPFQATMY  96
rGALR1   65  --PRSTTNLFILNLSIADLAYLLFCIPFQATMY  95
hGALR1   66  --PRSTTNLFILNLSIADLAYLLFCIPFQATMY  96
hGALR3.2 51  QEPGSTTDLFILNLAVADLCFILCCVPFQATIY  83
hGALR3.3 51  QEPRSTTDLFILNLAVADLCFILCCVPFQATIY  83
rGALR3    1  ---------------------------------   0
mGALR2   54  QAV-STTNLFILNLGVADLCFILCCVPFQATIY  85
rGALR2   55  QAV-STTNLFILNLGVADLCFILCCVPFQATIY  86
hGALR2   55  QAV-STTNLFILNLGVADLCFILCCVPFQATIY  86 mGALR1   97  ALPTWVLGAFICKFIHYFFTVSMLVSIFTLAAM  129
rGALR1   96  ALPTWVLGAFICKFIHYFFTVSMLVSIFTLAAM  128
hGALR1   97  ALPTWVLGAFICKFIHYFFTVSMLVSIFTLAAM  129
hGALR3.2 84  TLDAWLFGALVCKAVHLLIYLTMYASSFTLAAV  116
hGALR3.3 84  TLDAWLFGALVCKAVHLFIYLTMNASSFTLAAV  116
rGALR3    1  ---------------------------------    0
mGALR2   86  TLDDWVFGSLLCKAVHFLIFLTMHASSFTLAAV  118
rGALR2   87  TLDDWVFGSLLCKAVHFLIFLTMHASSFTLAAV  119
hGALR2   87  TLDDWVFGSLLCKAVHFLIFLTMHASSFTLAAV  119 mGALR1  130  SVDRYMAIVHSRRSSSLRVSRNALLGVGFIWAL  162
rGALR1  129  SVDRYMAIVHSRRSSSLRVSRNALLGVGFIWAL  161
hGALR1  130  SVDRYMAIVHSRRSSSLRVSRNALLGVGFIWAL  162
hGALR3.2 117 SVDRYLAVRHPLRSRALRTPRNARAAVGLVWLL  149
hGALR3.3 117 SVDRYLAVRHPLRSRALRTPRNARAAVGLVWLL  149
rGALR3    1  ---------------------------------    0
mGALR2  119  SLDRYLAIRYPMHSRELRTPRNALAAIGLIWGL  151
rGALR2  120  SLDRYLAIRYPMHSRELRTPRNALAAIGLIWGL  152
hGALR2  120  SLDRYLAIRYPMHSRELRTPRNALAAIGLIWGL  152
```

FIG. 5A

```
mGALR1    163  SIAMASPVAYHQRLFH-RDSNQTFCWEQWPNKL        194
rGALR1    162  SIAMASPVAYYQRLFH-RDSNQTFCWEHWPNQL        193
hGALR1    163  SIAMASPVAYHQGLFHPRASNQTFCWEQWPDPR        195
hGALR3.2  150  AALFSAP--YLSYYGTVRYGALELCVPAWEDAR        180
hGALR3.3  150  AALFSAP--YLSYYGTVRYGALELCVPAWEDAR        180
rGALR3      1  ------P--YLSYYGTVRYGRLELCVPAWEDAR         25
mGALR3    152  ALLFSGP--YLSYYSQSQLANLTVCHPAWSAPR        182
rGALR2    153  ALLFSGP--YLSYYSQSQLANLTVCHPAWSAPR        183
hGALR2    153  SLLFSGP--YLSYYRQSQLANLTVCHPAWSAPR        183 mGALR1    195  HKKAYVVCTFVFGYLLPLLLICFCYAKVLNHLH        227
rGALR1    194  HKKAYVVCTFVFGYLLPLLLICFCYAKVLNHLH        226
hGALR1    196  HKKAYVVCTFVFGYLLPLLLICFCYAKVLNHLH        228
hGALR3.2  181  RR-ALDVATFAAGYLLPVAVVSLAYGRTLRFLW        212
hGALR3.3  181  RR-ALDVATFAAGYLLPVAVVSLAYGRTLRFLW        212
rGALR3     26  RR-ALDVATFAAGYLLPVAVVSLAYGRTLCFLW         57
mGALR3    183  RR-AMDLCTFVFSYLLPVLVLSLTYARTLHYLW        214
rGALR2    184  RR-AMDLCTFVFSYLLPVLVLSLTYARTLHYLW        215
hGALR2    184  RR-AMDICTFVFSYLLPVLVLGLTYARTLRYLW        215 mGALR1    228  KKLKNM-SKKSEAS---KKKTAQTVLVMVVVFG        256
rGALR1    227  KKLKNM-SKKSEAS---KKKTAQTVLVMVVVFG        255
hGALR1    229  KKLKNM-SKKSEAS---KKKTAQTVLVMVVVFG        257
hGALR3.2  213  AAVGPAGAAAAEARRRATGRAGRAMLAVAALYA        245
hGALR3.3  213  AAVGPAGAAAAEARRRATGRAGRAMLAVAALYA        245
rGALR3     58  AAVGPAGSAAAEARRRATGRAGRRMLAVA-LYA         89
mGALR3    215  RTVDPV--AAGSGSQRAKRKVTRMIVIVAVLFC        245
rGALR2    216  RTVDPV--AAGSGSQRAKRKVTRMIIIVAVLFC        246
hGALR2    216  RAVDPV--AAGSGARRAKRKVTRMILIVAALFC        246 mGALR1    257  ISWLPHHVVHLWAEFGAFPLTPASFFFRITAHC        289
rGALR1    256  ISWLPHHVIHLWAEFGAFPLTPASFFFRITAHC        288
hGALR1    258  ISWLPHHIIHLWAEFGVFPLTPASFLFRITAHC        290
hGALR3.2  246  LCWGPHHALILCFWYGRFAFSPATYACRLASHC        278
hGALR3.3  246  LCWGPHHALILCFWYGRFAFSPATYACRLASHC        278
rGALR3     90  LCWGPHHALILCFWYGRFAFSPATYACRLASHC        122
mGALR3    246  LCWMPHHALILCVWFGRFPLTRATYALRILSHL        278
rGALR2    247  LCWMPHHALILCVWFGRFPLTRATYALRILSHL        279
hGALR2    247  LCWMPHHALILCVWFGQFPLTRATYALRILSHL        279 mGALR1    290  LAYSNSSVNPIIYAFLSENFRKAYKQVFKCHVC        322
rGALR1    289  LAYSNSSVNPIIYAFLSENFRKAYKQVFKCRVC        321
hGALR1    291  LAYSNSSVNPIIYAFLSENFRKAYKQVFKCHIR        323
hGALR3.2  279  LAYANSCLNPLVYALASRHFRARFRRLWPCGRR        311
hGALR3.3  279  LAYANSCLNPLVYALASRHFRARFRRLWPCGRR        311
rGALR3    123  LAYANSC-------------------------        129
mGALR3    279  VSYANSCVNPIVYALVSKHFRKGFRKI--CAGL        309
rGALR2    280  VSYANSCVNPIVYALVSKHFRKGFRKI--CAGL        310
hGALR2    280  VSYANSCVNPIVYALVSKHFRKGFRTI--CAGL        310
```

FIG. 5B

```
mGALR1    323  DESPRSETKENKSR--------- MDTPPSTNCT  346
rGALR1    322  NESPHGDAKE-KNR--------- IDTPPSTNCT  344
hGALR1    324  KDSHLSDTKENKSR--------- IDTPPSTNCT  347
hGALR3.2  312  RRHRARRALRRVRPASSGPPGCPGDARPSGRLL   344
hGALR3.3  312  RRHRARRALRRVRPASSGPPGCPGDARPSGTLL   344
rGALR3      0  ---------------------------------   129
mGALR2    310  LRRAPRRASGRVCILAPGNHSGGMLEPESTDLT   342
rGALR2    311  LRPAPRRASGRVSILAPGNHSGSMLEQESTDLT   343
hGALR2    311  LGRAPGRASGRVCAAARGTHSGSVLERESSDLL   343 mGALR1    347  HV ---------------------------  348
rGALR1    345  HV ---------------------------  346
hGALR1    348  HV ---------------------------  349
hGALR3.2  345  ----AGGGQGPEPREGPVHGGEAARGPE----- 368
hGALR3.3  345  ----AGGGQGPEPREGPVHGGEAARGPE----- 368
rGALR3      0  ------------------------------   129
mGALR2    343  QVSEAAGPLVPAPA----- LPNCTTLSRTLDP  369
rGALR2    344  QVSEAAGPLVPPPA----- LPNCTASSRTLDP  370
hGALR2    344  HMSEAAGALRPCPGASQPCILEPCPGPSWQGPK  376 mGALR1      0  -----------  348
rGALR1      0  -----------  346
hGALR1      0  -----------  349
hGALR3.2    0  -----------  368
hGALR3.3    0  -----------  368
rGALR3      0  -----------  129
mGALR2    370  AC---------  371
rGALR2    371  AC---------  372
hGALR2    377  AGDSILTVDVA  387
```

FIG. 5C

```
CCCTACCTCAGCTACTACGGCACGGTGCGCTACGGCCGGCTCGA
GCTCTGCGTGCCCGCTTGGGAGGACGCGCGGCGGCGCGCGCTGG
ACGTGGCCACCTTCGCCGCGGGCTACCTGCTGCCGGTGGCCGTG
GTGAGCCTGGCCTACGGACGCACGCTATGTTTCCTATGGGCCGCC
GTGGGTCCCGCGGGCAGCGCGGCAGCAGAGGCGCGCAGACGGG
CGACCGGCCGGGCGGGACGCCGCATGCTGGCAGTGGCGCTCTAC
GCGCTTTGCTGGGGCCCGCACCACGCGCTCATCCTCTGCTTCTGG
TACGGTCCGTTCGCCTTCAGCCCGGCCACCTACGCCTGTCGCCTG
GCCTCACACTGCCTCGCCTACGCCAACTCCTGC
```

FIG.8

PYLSYYGTVRYGRLELCVPAWEDARRRALDVATFAAGYLLPVAVV
SLAYGRTLCFLWAAVGPAGSAAAEARRRATGRAGRRMLAVALYA
LCWGPHHALILCFWYGPFAFSPATYACRLASHCLAYANSC

FIG.9

NUCLEOTIDE ENCODING HUMAN GALANIN RECEPTOR 3 (GALR3)

CROSS-REFERENCE TO RELATED APPLICATIONS

This application is a continuation of PCT/US98/26812, international filing date of Dec. 17, 1998, which claims priority to U.S. Serial No. 60/069,725, filed Dec. 17, 1997, now abandoned. The entirety of these applications are hereby incorporated by reference herein.

STATEMENT REGARDING FEDERALLY-SPONSORED R&D

Not applicable

REFERENCE TO MICROFICHE APPENDIX

Not applicable

FIELD OF THE INVENTION

This invention relates to a novel galanin receptor, designated GALR3, to nucleotides encoding same, and to assays making use thereof.

BACKGROUND OF THE INVENTION

Although first isolated from porcine intestine, galanin is widely distributed in the central and peripheral nervous system. Galanin in most species is a 29 amino acid peptide with an amidated carboxyl terminus. Human galanin is unique in that it is longer, 30 amino acids, and is not amidated. There is strong conservation of the galanin sequence with the amino terminal fifteen residues being absolutely conserved in all species. Galanin immunoreactivity and binding is abundant in the hypothalamus, the locus coeruleus, the hippocampus and the anterior pituitary, as well as regions of the spinal cord, the pancreas and the gastrointestinal tract.

Like neuropeptide Y (NPY), injection of galanin into the paraventricular nucleus (PVN) of the hypothalamus produces a dose-dependent increase in feeding in satiated rats. While galanin, like norepinephrine, enhances carbohydrate ingestion, some studies have shown that it profoundly increases fat intake. It has been suggested that galanin shifts macronutrient preference from carbohydrate to fat. The same injections that increase feeding reduce energy expenditure and inhibit insulin secretion. There is enhanced galanin expression in the hypothalamus of genetically obese rats compared with their lean littermate controls. Injection of peptide receptor antagonists into the PVN blocks the galanin-specific induction of increased fat intake. Specific galanin antisense oligonucleotides when injected into the PVN produce a specific decrease in galanin expression associated with a decrease in fat ingestion and total caloric intake while hardly affecting either protein or carbohydrate intake. Thus galanin appears to be one potential neurochemical marker related to the behavior of fat ingestion.

Galanin inhibits cholinergic function and impairs working memory in rats. Lesions that destroy cholinergic neurons result in deficits in spatial learning tasks. While locally administered acetylcholine (ACh) reverses some of this deficit, galanin blocks this ACh-mediated improvement. Evidence from autopsy samples from Alzheimer's disease-afflicted brains suggests an increased galinergic innervation of the nucleus basilis. Thus, if galinergic overactivity contributes to the decline in cognitive performance in Alzheimer's disease, galanin antagonists may be therapeutically useful in alleviating cognitive impairment.

In the rat, administration of galanin intracerebroventricularly, subcutaneously or intravenously increases plasma growth hormone. Infusion of human galanin into healthy subjects also increases plasma growth hormone and potently enhances the growth hormone response to GHRH.

Galanin levels are particularly high in dorsal root ganglia. Sciatic nerve resection dramatically up-regulates galanin peptide and mRNA levels. Chronic administration of galanin receptor antagonists (M35, M15) after axotomy results in a marked increase in self mutilation behavior in rats, generally considered to be a response to pain. Application of antisense oligonucleotides specific for galanin to the proximal end of a transected sciatic nerve suppressed the increase in galanin peptide levels with a parallel increase in autotomy. Galanin injected intrathecally acts synergistically with morphine to produce analgesia, this antinociceptive effect of morphine is blocked by galanin receptor antagonists. Thus, galanin agonists may have some utility in relieving neural pain.

The actions of galanin are mediated by high affinity galanin receptors that are coupled by pertussis toxin sensitive $G_i/G_o$ proteins to inhibition of adenylate cyclase activity, closure of L-type $Ca^{++}$ channels and opening of ATP-sensitive $K^+$ channels. Specific binding of $^{125}I$-galanin (Kd approximately 1 nM) has been demonstrated in areas paralleling localization of galanin immunoreactivity: hypothalamus, ventral hippocampus, basal forebrain, spinal cord, pancreas and pituitary. In most tissues the amino terminus (GAL 1–15) is sufficient for high affinity binding and agonist activity.

Recently, a galanin receptor cDNA was isolated by expression cloning from a human Bowes melanoma cell line. (Habert-Ortoli, et al. 1994. *Proc. Nat. Acad. Sci, USA* 91: 9780–9783). This receptor, GALR1, is expressed in human fetal brain and small intestine, but little else is known of its distribution. Gal(1–16) is at least 1000 times more active than pGAL(3–29) as an inhibitor of $^{125}I$-porcine galanin binding to this receptor transiently expressed in COS cells. It remains to be determined whether this receptor subtype represents the hypothalamic receptor that mediates the galanin specific feeding behavior.

It would be desirable to identify further galanin receptors so that they can be used to further characterize this biological system and to identify galanin receptor subtype selective agonists and antagonists.

SUMMARY OF THE INVENTION

This invention relates to a novel galanin receptor, designated GALR3, substantially free from associated proteins, and to GALR3-like receptors which are at least about 40% homologous and which have substantially the same biological activity. In preferred embodiments of this invention, the GALR3-like receptors are at least about 60%, and more preferably at least about 75%, and even more preferably at least about 85% homologous to a GALR3 receptor. This invention also relates specifically to rat, human and mouse GALR3, substantially free from associated proteins, and to receptors which are at least about 50% homologous and which have substantially the same biological activity.

Another aspect of this invention are primate and non-primate GALR3 proteins which are encoded by substantially the same nucleic acid sequences, but which have undergone changes in splicing or other RNA processing-derived modifications or mutagenesis-induced changes, so that the expressed protein has a homologous, but different amino acid sequence from the native forms. These variant forms may have different and/or additional functions in human and animal physiology or in vitro in cell based assays.

A further aspect of this invention are nucleic acids which encode a GALR3 receptor, a GALR3-like receptor or a functional equivalent of a GALR3 receptor from rat, human, mouse, swine, or other species. These nucleic acids may be free from associated nucleic acids, or they may be isolated or purified. The nucleic acids which encode a receptor of this invention may be any type of nucleic acid. Preferred forms are DNAs, including genomic and cDNA, although this invention specifically includes RNAs as well. Nucleic acid constructs may also contain regions which control transcription and translation such as one or more promoter regions, termination regions, and if desired enhancer regions. The nucleic acids may be inserted into any known vector including plasmids, and used to transfect suitable host cells using techniques generally available to one of ordinary skill in the art.

Another aspect of this invention are vectors comprising nucleic acids which encode GALR3, and host cells which contain these vectors. Still another aspect of this invention is a method of making GALR3 comprising introducing a vector comprising nucleic acids encoding GALR3 into a host cell under culturing conditions.

Yet another aspect of this invention are assays for GALR3 ligands which utilize the receptors and/or nucleic acids of this invention. Preferred assays of this embodiment compare the binding of the putative GALR3 ligand to the binding of galanin to GALR3.

BRIEF DESCRIPTION OF THE DRAWINGS

FIG. 1 is the DNA sequence of human GALR3 gene, clone GALR3—3 (SEQ ID NO:1).

FIG. 2 is the deduced amino acid sequence of human GALR3, clone GALR3—3 (SEQ ID NO:2).

FIG. 3 is the DNA sequence (open reading frame only) of human GALR3, clone GALR3-2 (SEQ ID NO:3).

FIG. 4 is the deduced amino acid sequence of GALR3, clone GALR3-2 (SEQ ID NO:4)

FIG. 5 is a comparison of the open reading frame protein sequences of human and rat GALR3 with the corresponding sequences of GALR1 (mouse—SEQ ID NO:5, rat—SEQ ID NO:6, and human—SEQ ID NO:7) and GALR2 (mouse—SEQ ID NO:8, rat—SEQ ID NO:9, and human—SEQ ID NO:10).

FIG. 8 is the DNA sequence of rat GALR3 from region TM4 to region TM7 (SEQ ID NO:11).

FIG. 9 is the deduced amino acid sequence of rat GALR3 from region TM4 to region TM7 (SEQ ID NO:12).

DETAILED DESCRIPTION OF THE INVENTION

Figure 6:
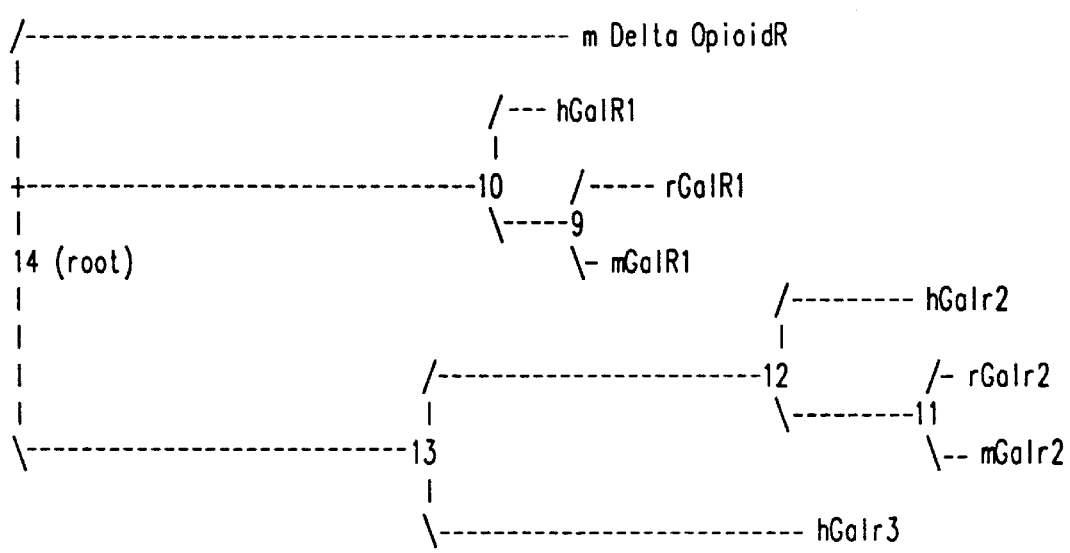
FIG. 6 is a phylogenetic analysis of the putative GALR3 protein sequence.

As used throughout the specification and claims, the following definitions apply:

"Substantially free from associated proteins" means that the receptor is at least about 90%, and preferably at least about 95% free from other cell membrane proteins which are normally found in a living mammalian cell which expresses a galanin receptor.

"Substantially free from associated nucleic acids" means that the nucleic acid is at least about 90%, and preferably at least about 95%, free from other nucleic acids which are normally found in a living mammalian cell which naturally expresses a galanin receptor gene.

"Substantially the same biological activity" means that the receptor-galanin binding constant is within 5-fold of the binding constant of GALR3 and galanin, and preferably within 2-fold of the binding constant of GALR3 and galanin.

"Stringent post-hybridizational washing conditions" means 0.1×standard saline citrate (SSC) at 65° C.

"Standard post-hybridizational washing conditions" means 6×SSC at 55° C.

"Relaxed post-hybridizational washing conditions" means 6×SSC at 30° C., or 1 to 2×SSC at 55° C.

"Functional equivalent" means that a receptor which does not have the exact same amino acid sequence of a naturally occurring GALR3 protein due to alternative splicing, deletions, mutations, or additions, but retains at least 1%, preferably 10%, and more preferably 25% of the biological activity of the naturally occurring receptor. Such derivatives will have a significant homology with a natural GALR3 and can be detected by reduced stringency hybridization with a DNA sequence obtained from a GALR3. The nucleic acid encoding a functional equivalent has at least about 60% homology at the nucleotide level to a naturally occurring receptor nucleic acid.

It has been found, in accordance with this invention, that there is a third galanin receptor, which is designated GALR3. The human (clone 3—3 and 3-2) and rat GALR3 sequences are given in FIGS. 1, 3 and 8, respectively, and are referenced in the Examples; however it is to be understood that this invention specifically includes GALR3 without regard to the species and, in particular, specifically includes rodent (including rat and mouse), rhesus, swine, chicken, cow and human. The galanin 3 receptors are highly conserved throughout species, and one of ordinary skill in the art, given the rat, human and/or mouse sequences presented herein, can easily design probes to obtain the GALR3 from other species.

GALR3 proteins contain various functional domains, including one or more domains which anchor the receptor in the cell membrane, and at least one ligand binding domain. As with many receptor proteins, it is possible to modify many of the amino acids, particularly those which are not found in the ligand binding domain, and still retain at least a percentage of the biological activity of the original receptor. Thus this invention specifically includes modified functionally equivalent GALR3s which have deleted, truncated, or mutated N-terminal portions. This invention also specifically includes modified functionally equivalent GALR3s which contain modifications and/or deletions in other domains, which are not accompanied by a loss of functional activity.

Additionally, it is possible to modify other functional domains such as those that interact with second messenger effector systems, by altering binding specificity and/or selectivity. Such functionally equivalent mutant receptors are also within the scope of this invention.

The proteins of this invention were found to have structural features which are typical of the 7-transmembrane domain (TM) containing G-protein linked receptor superfamily (GPC-R's or 7-TM receptors). Thus GALR3 proteins make up new members of the GPC-R family of receptors. The intact GALR3 of this invention was found to have the general features of GPC-R's, including seven transmembrane regions, three intra- and extracellular loops, and the GPC-R protein signature sequence. The TM domains and GPC-R protein signature sequence are noted in the protein sequences of the GALR3. Not all regions are required for functioning, and therefore this invention also comprises functional receptors which lack one or more non-essential domains.

Determination of the nucleotide sequence indicated that the GALR3 belongs to the intron-containing class of GPC-R's.

The DNA sequence encoding the putative GALR3 is shown in FIGS. 1 and 3. The human putative GALR3 gene is organized similarly to human GALR2 with a single intron (~1 kb) dividing the open reading into two exons with Exon 1 consisting of ~350 bp, and Exon 2~700 bp. Based on database searching, the open reading frame protein sequence for this novel gene (FIGS. 2 and 4) is most closely related to GALR2 and GALR1 with 58, 75% identity and similarity to human GALR2, and 37, 61% identity and similarity to rat GALR1 (FIG. 5). Differences in open reading frame DNA sequence and the resulting deduced amino acid sequence between clone GALR3–2 and GALR3—3 may be allelic in nature. Phylogenetic analysis of the putative GALR3 protein sequence supports the notion that this gene encodes a receptor for galanin (FIG. 6).

The human GALR3 protein bears strong sequence identity and similarity to the rat GALR3 ortholog.

This invention also relates to truncated forms of GALR3, particularly those which encompass the extracellular portion of the receptor, but lack the intracellular signaling portion of the receptor, and to nucleic acids encoding these truncated forms. Such truncated receptors are useful in various binding assays. Thus this invention specifically includes modified functionally equivalent GALR3s which have deleted, truncated, or mutated N-terminal portions. This invention also specifically includes modified functionally equivalent GALR3s including receptor chimeras which contain modifications and/or deletions in other domains, which are not accompanied by a loss of functional activity.

Additionally, it is possible to modify other functional domains such as those that interact with second messenger effector systems, by altering binding specificity and/or selectivity. Such functionally equivalent mutant receptors are also within the scope of this invention.

Assays which make up further aspects of this invention include binding assays (competition for $^{125}$I-galanin binding), coupling assays (including galanin-mediated inhibition of forskolin-stimulated adenylate cyclase in cells expressing galanin receptors), measurement of galanin-stimulated calcium release in cells expressing galanin receptors (such as aequorin assays), stimulation of inward rectifying potassium channels (GIRK channels, measured by voltage changes) in cells expressing galanin receptors, and measurement of pH changes upon galanin stimulation of cells expressing galanin receptors as measured with a microphysiometer.

Host cells may be cultured under suitable conditions to produce GALR3. An expression vector containing DNA encoding the receptor may be used for expression of receptor in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to Drosophila, Spodoptera, and silkworm derived cell lines. Cell lines derived from mammalian species which are suitable and which are commercially available include, but are not limited to, L cells L-M(TK$^-$) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The specificity of binding of compounds showing affinity for the receptor is shown by measuring the affinity of the compounds for cells transfected with the cloned receptor or for membranes from these cells. Expression of the cloned receptor and screening for compounds that inhibit the binding of radiolabeled ligand to these cells provides a rational way for rapid selection of compounds with high affinity for the receptor. These compounds identified by the above assays may be agonists or antagonists of the receptor and may be peptides, proteins, or non-proteinaceous organic molecules. Alternatively, functional assays of the receptor may be used to screen for compounds which affect the activity of the receptor. Such functional assays range from ex vivo muscle contraction assays to assays which determine second messenger levels in cells expressing the receptor. The second messenger assays include, but are not limited to, assays to measure cyclic AMP or calcium levels or assays to measure adenyl cyclase activity. These compounds identified by the above assays may be agonists, antagonists, suppressors, or inducers of the receptor. The functional activity of these compounds is best assessed by using the receptor either natively expressed in tissues or cloned and exogenously expressed.

Using the assays of this invention, galanin agonists and antagonists may be identified. A galanin agonist is a compound which binds to the GALR3, such as a galanin mimetic, and produces a cellular response which is at least about equivalent to that of galanin, and which may be greater than that of galanin. Such compounds would be useful in situations where galanin insufficiency causes anorexia, or for treatment of pain.

Also using this embodiment of the assay, galanin antagonists may be identified. A galanin antagonist is a compound which can bind to the GALR3, but produces a lesser response than that of native galanin. Such compounds would be useful in the treatment of obesity.

One assay of this invention is a method of identifying a compound which modulates GALR3 receptor comprising: a) culturing cells expressing the GALR3 receptor in the presence of the compound and b) measuring GALR3 receptor activity or second messenger activity. If desired, the determined activity can be compared to a standard, such as that measured using galanin as the compound. In preferred embodiments, the cells are transformed and express the GALR3 receptor.

The consultant cDNA clone (or shorter portions of, for instance, only 15 nucleotides long) may be used to probe libraries under hybridization conditions to find other receptors which are similar enough so that the nucleic acids can hybridize, and is particularly useful for screening libraries from other species. In this step, one of ordinary skill in the art will appreciate that the hybridization conditions can vary from very stringent to relaxed. Proper temperature, salt concentrations, and buffers are well known.

The following non-limiting Examples are presented to better illustrate the invention.

EXAMPLE 1

Human GALR3
Identification and Cloning of Human GalR3 Gene, Sequence and Gene Structure Automated searching of sequence data from GenBank (National Center For Biotechnology Information, Bethesda, Md.) were queried using sequences from known receptor clones. Using a list of 50–60 rhodopsin family amino acid sequences, the NEW division of GenBank was searched. The query algorithm is TFASTX and the output is placed in a file where alignments are sorted by query sequence and scored (cut-off based on the expectation value, set for example, at 0.01). A DNA sequence alignment of 300 bp to a portion of a large BAC clone (~100,000 bp) with accession number Z97630 was identified from the high through-put genomic sequence (HTGS database, GenBank). The complete open reading frame (ORF) for the putative gene encoding GALR3 was then identified using sequence from BAC Z97630 and an additional BAC clone, with assession number Z82241, from the HTGS database. The Genbank assession numbers corresponded to the following HTGS BAC clones (HS entries): Z97630, HS466N1; Z82241, HS8112.

DNA sequences derived from these BACs were used to choose PCR primers. PCR primers begining at the predicted initiating Met and ending more 3' than the predicted stop codon were utilized to PCR from human genomic DNA a fragment containing the predicted Exon I, the intervening intron, and predicted Exon II. This PCR product was subcloned and sequenced, resulting in expression plasmid GALR3— 3.

In a parallel approach, a human genomic DNA library (Stratagene, La Jolla, Calif.) was screened to isolate the putative GALR3 gene. Primary screening under medium stringency resulted in 6 positive plaques using an Exon 2 probe. One hybridizing phage plaque was obtained upon secondary screening. A 13 kb EcoR1/EcoRV fragment was identified from the genomic clone by Southern blotting, transferred into pBluescript vector (Stratagene, La Jolla, Calif.), and confirmed to be GALR3 by sequencing. A intronless GALR3 expression construct was assembled in a similar manner to that described above using Pfu DNA polymerase (Stratagene, La Jolla, Calif.) resulting in expression plasmid GALR3–2.

EXAMPLE 2

Chromosomal Location

The BAC clones which were identified by the searches of the HTGS dataset have been mapped by the The Sanger Centre (Cambridge, UK) genome research laboratory to human chromosome 22. FISH analysis conducted herein has confirmed this assignment and refined it to 22q12.2–13.1.

EXAMPLE 3

Receptor Expression
Construction of Human GalR3 Expression Plasmid

The human GalR3 cDNA expression construct was assembled stepwise from PCR products amplified from human genomic DNA. Each exon was PCR amplified using standard conditions. The primers in for exon I were: Forward Exon I (5'-gcg aat tcg gta cca tgg ctg atg ccc aga aca t-3'; SEQ ID NO:13) and Reverse Exon I (5'-cgc ctg tcg aca gat aca gca gc -3'; SEQ ID NO:14). The primers for exon II were: Forward Exon II (5'-tgt atc tgt cga cag gta acc tgg ccg tgc ggc acc c-3'; SEQ ID NO:15) and Reverse Exon II (5'-gcg cgg ccg ctt att ccg gtc ctc ggg c-3'; SEQ ID NO:16). PCR products were subcloned into pCRII and sequenced. For expression in mammalian cells, the putative GALR3 ORF was subcloned into pcDNA-1/amp (Invitrogen) resulting in plasmid GALR3—3; and pcDNA-3 (Invitrogen), resulting in plasmid GALR3–2.

EXAMPLE 4

RNA Expression Profile

Using RNase protection analysis, the relative levels of human GALR3 mRNA was assessed. As shown below GALR3 is expressed in numerous brain regions and peripheral tissues, as observed for GALR1 and GALR2.

| Tissue | Expression Level |
| --- | --- |
| Amygdala | + |
| Cerebellum | + |
| Frontal Cortex | + |
| Hippocampus | + |
| Hypothalamus | ++ |
| Pituitary | + |
| Brain stem | + |
| Lung | ++ |
| Heart | + |
| Spleen | + |
| Liver | + |
| Pancreas | + |
| Duodenum | + |
| Colon | + |
| Straited muscle | ++ |

EXAMPLE 5

Radioligand Binding
Pharmacology of Human GALR3

Mammalian COS-7 cells were transfected by electroporation. COS-7 cells ($1 \times 10^7$) were suspended in 0.85 ml of Ringers' buffer and 15 mg of the GALR3–2 or GALR3—3 expression plasmid was added to a 0.4 mm electroporation cuvette (Bio-Rad, Hercules, Calif.). Current was applied (960 mF, 260 V) using a Bio-Rad Electroporator device and the cells were transferred to a T-180 flask (Corning). Expression was allowed to proceed for 72 hrs.

Membranes were prepared from transfected cells following dissociation in enzyme-free dissociation solution (Specialty Media, Lavallette, N.J.) by disruption in a Dounce homogenizer in ice-cold membrane buffer (10 mM Tris, pH 7.4, 10 mM PMSF, 10 mM phosphoramidon, and 40 mg/ml bacitracin). After a low speed (1100×g for 10 min. at 4° C.) and a high speed centrifugation (38,700×g for 15 min. at 4° C.), membranes were resuspended in buffer and protein concentration determined (Bio-Rad assay kit). Binding of $^{125}$I-human or porcine galanin (specific activity of 2200 Ci/mmol, DuPont NEN) was measured in membranes using a buffer of 25 mM Tris pH 7.4, 0.5% BSA, 2 mM $MgCl_2$, 40 $\mu$g/ml bacitracin, 4 mg/ml phosphoramidon, and 10 $\mu$M leupeptin in a total volume of 250 ml. 70 $\mu$M $^{125}$I-human or porcine galanin was used. Transfected cells expressing plasmid GALR3—3 were bound with $^{125}$I-human galanin whereas cells expressing plasmid GALR3–2 were bound with $^{125}$I-porcine galanin. Reactions were initiated by the addition of membranes and the incubation was allowed to proceed at room temperature for 1 hour. Non-specific binding was defined as the amount of radioactivity remaining bound in the presence of 1 mM respectively unlabeled galanin and was generally not above 200 cpm (<10% of total radioactivity bound). Titration of membrane protein from 1 to 50 $\mu$g was conducted. In competition studies various concentrations of unlabeled human or porcine galanin were included along with $^{125}$I-porcine galanin (70 pM) in cells expressing the GALR3–2 plasmid. Incubations were terminated by rapid filtration through GF/C filters which had been presoaked with 0.1% polyethylamine using a TOMTEC (Orange, Conn.) cell harvester. The results were analyzed using the Prism software package (GraphPad, San Diego, Calif.). The table below illustrates that both clones confer specific binding to COS-7 cells for both human and porcine galanin radioligands as a function of protein concentration. In COS-7 cells mock transfected with expression vector only (no GALR3 gene), no specific binding of either radioligand was observed.

| Membrane Protein (µg) | Clone GALR3-3 $^{125}$I-human galanin (cpm) | Clone GALR3-2: $^{125}$I-porcine galanin (cpm) |
| --- | --- | --- |
| 1 | ND | ND |
| 5 | 211 | 695 |
| 10 | 407 | 1134 |
| 20 | 886 | 1763 |
| 50 | 2061 | 3728 |

Figure 7:
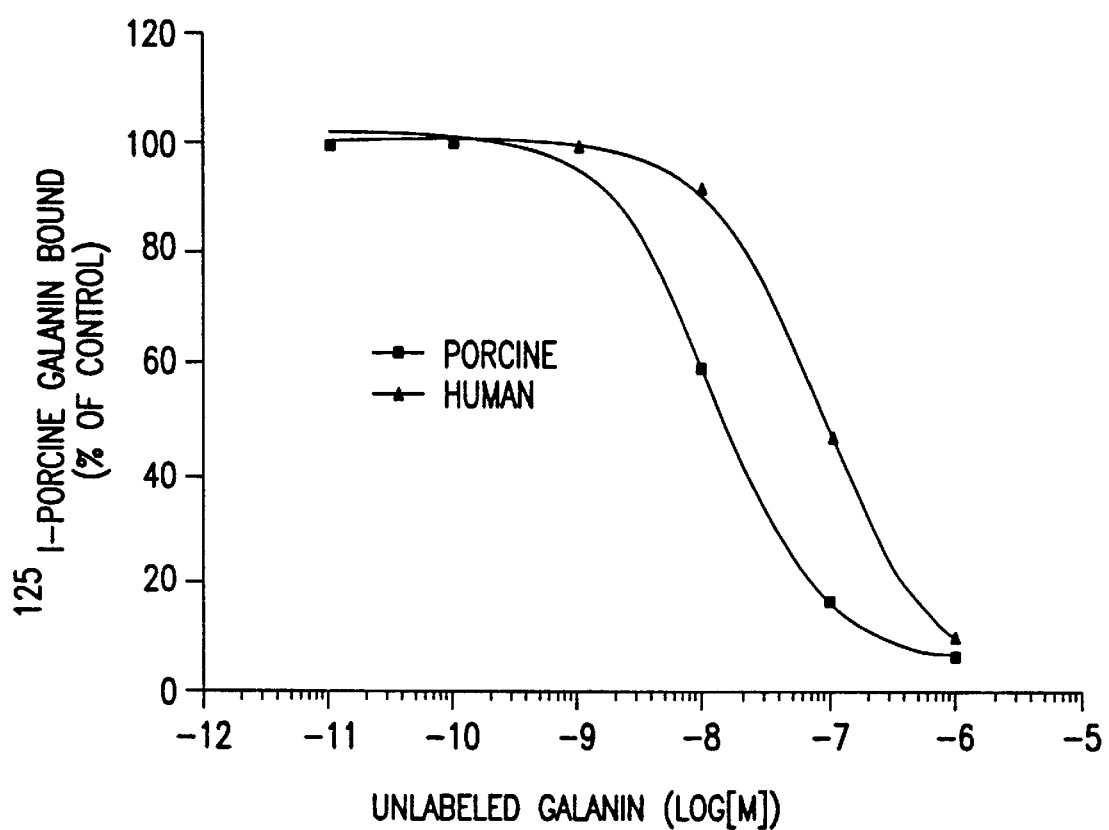
FIG. 7 illustrates the competition curves for $^{125}$I-porcine glanin against human and porcine galanin.

Competition curves for $^{125}$I-porcine galanin against human and porcine galanin were generated to to determine the IC50 for both unlabeled peptides (clone GALR3–2), as shown in FIG. 7. The IC50 values for porcine and human galanin were 16 nM and 93 nM, respectively.

EXAMPLE 6

Rat GALR3

Identification and Cloning of Rat GalR3 Gene

Primers based on the intronless human GALR3 sequence from TM4 and TM7 were designed and used to PCR amplify with Pfu DNA polymerase the rat GALR3 ortholog from rat genomic DNA. A PCR product of the appropriate size (approximately 400 bp) that hybridized with an Exon 2 probe from the human GALR3 gene was subcloned into pBluescript vector (Stratagene, La Jolla, Calif.). The DNA sequence is shown is FIG. 8 and the deduced amino acid sequence is shown in FIG. 9. DNA sequence analysis revealed significant homology with human GALR3: approximately 95% protein sequence identity for 129 amino acids spanning TM4 through TM-7.

RNA Expression

Northern blot analysis using a probe dervived from the rat GALR3 ORF has revealed expression of rat GALR3 mRNA in hypothalamus, mid-brain, pons, and whole fetal brain.

What is claimed:

1. An isolated nucleic acid molecule comprising a sequence of nucleotides that encodes a human galanin receptor 3 (GALR3) protein as set forth in SEQ ID NO:2.

2. The isolated nucleic acid molecule of claim 1 wherein the nucleic acid is DNA.

3. The isolated nucleic acid molecule of claim 1 wherein the nucleic acid is mRNA.

4. The isolated nucleic acid molecule of claim 1 wherein the nucleic acid is cDNA.

5. The isolated nucleic acid molecule of claim 1 wherein the sequence of nucleotides comprises the sequence of nucleotides set forth in SEQ ID NO:1.

6. A vector comprising the nucleic acid molecule of claim 1.

7. A host cell comprising the vector of claim 6.

8. A process for expressing a human galanin receptor 3 (GALR3) protein in a recombinant host cell, comprising:

(a) introducing a vector comprising the nucleic acid molecule of claim 1 into a suitable host cell; and, (b) culturing the host cell under conditions which allow expression of said human GALR3 protein.

* * * * *

UNITED STATES PATENT AND TRADEMARK OFFICE
CERTIFICATE OF CORRECTION

PATENT NO. : 6,511,827 B1
DATED : January 28, 2003
INVENTOR(S) : Andrew D. Howard et al.

It is certified that error appears in the above-identified patent and that said Letters Patent is hereby corrected as shown below:

Title page,
Item [73], Assignee, delete "Merck & Co., Inc., Rahway, NJ (US)" and insert
-- Merck & Co., Inc., Rahway, NJ (US) and University of Virginia Patent Foundation, Charlottesville, VA (US) --

Signed and Sealed this

Fourth Day of May, 2004

JON W. DUDAS
*Acting Director of the United States Patent and Trademark Office*

SEQUENCE LISTING

<160> NUMBER OF SEQ ID NOS: 16

<210> SEQ ID NO 1
<211> LENGTH: 2263
<212> TYPE: DNA
<213> ORGANISM: human

<400> SEQUENCE: 1

```
ccaggtcggg ggagttagat cccggggtca agcaaccaga actgggggct cttgcctgag      60
gattccagct tctcttccca ggtgcccgtc tgatggggag atggctgatg cccagaacat     120
ttcactggac agcccaggga gtgtgggggc cgtggcagtg cctgtggtct ttgccctaat     180
cttcctgctg ggcacagtgg gcaatgggct ggtgctggca gtgctcctgc agcctggccc     240
gagtgcctgg caggagcctc gcagcaccac ggacctgttc atcctcaacc tggcggtggc     300
tgacctctgc ttcatcctgt gctgcgtgcc cttccaggcc accatataca cgctggatgc     360
ctggctcttt ggggccctcg tttgcaaggc cgtgcacctg ttcatctacc tcaccatgaa     420
cgccagcagc tttcgctgg ctgctgtatc tgtggacagg tgcgctgtgc ctggggcctg     480
gctgggcagg gctgtggggg cggggttgg gggaggagtc ctgaacagat cctcactggc     540
cttaggaagg agagagtggg ggaccagaaa gggaggtggg tgggaggaaa caaaagctcc     600
ctgacccctc gcaagcagcc tctgggcacc tgcagggcgt gcttgagggg actgtcctgc     660
ccttcccctc ctccactgtg aacttccaga ggacgcctct gagtctcaag tggcagcaca     720
gggtctggca catagtaagt gctctgtaag cgcgaaatga atcgcaaaag aagctcacga     780
atgcgttcat cagtttttt gttttgtttt gttttgttgt ttttttttt ttggatcttg     840 gctcactgca acctctgcct cctgggttcc agcgattctc ctgccacagc ctcctgagta     900
gctgggatta caggccacca cacctggcta atttttgta ttttagtag aaacgggtt       960
```

-continued

```
ttgccatgtt ggacaggctg gtctcgaacc cctgacctca agtgatccgc ccgcctcggc    1020
ctcccaagtg ctgggattac aggcgtgagc caccgcgccc agcccagcta ttttctaact    1080
gcccacacct ggccaagctg tgcacacatc tgcttccaca gcttgaaact ggggtcaaa     1140 tccaggctca ctccagctga tgaccctggg caagtcactt ctctctggac ctcatctgac    1200
gcatccataa aataatccta gaaataacaa gtcaccggga tcgggccctt gctaggtgca    1260
agggcctaag caccttgcgc gttcacaccc ttaatccccg ccacgtcccc cacggttcac    1320
aggaggcgca ctgggccgca gggcccgggc gcgggacgtg gcgcgggccc ctgcgggagg    1380
gcacctgccc gccccgctga ccasgcgccc tccgcaggta cctggccgtg cggcacccgc    1440
tgcgctcgcg cgccctgcgc acgccgcgta acgcccgcgc cgcagtgggg ctggtgtggc    1500
tgctggcggc gctcttctcg gcgccctacc tcagctacta cggcaccgtg cgctacggcg    1560
cgctggagct ctgcgtgccc gcctgggagg acgcgcgccg ccgcgccctg acgtggccca    1620
ccttcgctgc cggctacctg ctgcccgtgg cygtggtgag cctggcctac gggcgcacgc    1680
tgcgcttcct gtgggccgcc gtgggtcccg cgggcgcggc ggcrgccaar gcgcggcgga    1740
gggcgackgg ccgcgcgggg cgcgccatgc tggcggtggc cgcgctctac gcgctmtgct    1800
ggggtccgca ccacgcgctc atcctgtgct tctggtacgg ccgmttcgcc ttcagcccgg    1860
ccacctacgc mtgccgcctg gcctcacact gcctggccta cgccaactcm tgcctcaacc    1920
cgctcgtmta cgcgctcgcc tcgcgccact tccgcgcgcg cttccgccgc ctgtggccgt    1980
gcggycgccg acgccgccac cgtgcccgcc gcgccttgcg tcgcgtccgc cccgcgtcct    2040
cgggcccacc cggctgcccc ggagacgccc ggcctagcgg gacgctgctg gctggtggcg    2100
gccagggccc sgagcccagg gagggacccg tccacgcgcg agaggctgcc cgaggaccgg    2160
aataaaccct gccgcctgga ctccgcctgt gtccgtctgt ctcactcccg ttctccgaag    2220
gcgggacgcc accgggccag ggatggggca atgccacgag ctc                      2263
```

<210> SEQ ID NO 2
<211> LENGTH: 368
<212> TYPE: PRT
<213> ORGANISM: human

<400> SEQUENCE: 2

```
Met Ala Asp Ala Gln Asn Ile Ser Leu Asp Ser Pro Gly Ser Val Gly
 1               5                  10                  15

Ala Val Ala Val Pro Val Val Phe Ala Leu Ile Phe Leu Leu Gly Thr
                20                  25                  30

Val Gly Asn Gly Leu Val Leu Ala Val Leu Leu Gln Pro Gly Pro Ser
            35                  40                  45

Ala Trp Gln Glu Pro Arg Ser Thr Thr Asp Leu Phe Ile Leu Asn Leu
        50                  55                  60

Ala Val Ala Asp Leu Cys Phe Ile Leu Cys Cys Val Pro Phe Gln Ala
 65                  70                  75                  80

Thr Ile Tyr Thr Leu Asp Ala Trp Leu Phe Gly Ala Leu Val Cys Lys
                85                  90                  95

Ala Val His Leu Phe Ile Tyr Leu Thr Met Asn Ala Ser Ser Phe Thr
                100                 105                 110

Leu Ala Ala Val Ser Val Asp Arg Tyr Leu Ala Val Arg His Pro Leu
            115                 120                 125

Arg Ser Arg Ala Leu Arg Thr Pro Arg Asn Ala Arg Ala Ala Val Gly
        130                 135                 140
```

```
Leu Val Trp Leu Leu Ala Ala Leu Phe Ser Ala Pro Tyr Leu Ser Tyr
145                 150                 155                 160

Tyr Gly Thr Val Arg Tyr Gly Ala Leu Glu Leu Cys Val Pro Ala Trp
                165                 170                 175

Glu Asp Ala Arg Arg Ala Leu Asp Val Ala Thr Phe Ala Ala Gly
            180                 185                 190

Tyr Leu Leu Pro Val Ala Val Val Ser Leu Ala Tyr Gly Arg Thr Leu
            195                 200                 205

Arg Phe Leu Trp Ala Ala Val Gly Pro Ala Gly Ala Ala Ala Lys
210                 215                 220

Ala Arg Arg Arg Ala Thr Gly Arg Ala Gly Arg Ala Met Leu Ala Val
225                 230                 235                 240

Ala Ala Leu Tyr Ala Leu Cys Trp Gly Pro His His Ala Leu Ile Leu
                245                 250                 255

Cys Phe Trp Tyr Gly Arg Phe Ala Phe Ser Pro Ala Thr Tyr Ala Cys
                260                 265                 270

Arg Leu Ala Ser His Cys Leu Ala Tyr Ala Asn Ser Cys Leu Asn Pro
            275                 280                 285

Leu Val Tyr Ala Leu Ala Ser Arg His Phe Arg Ala Arg Phe Arg Arg
            290                 295                 300

Leu Trp Pro Cys Gly Arg Arg Arg His Arg Ala Arg Arg Ala Leu
305                 310                 315                 320

Arg Arg Val Arg Pro Ala Ser Ser Gly Pro Gly Cys Pro Gly Asp
                325                 330                 335

Ala Arg Pro Ser Gly Thr Leu Leu Ala Gly Gly Gln Gly Pro Glu
            340                 345                 350

Pro Arg Glu Gly Pro Val His Gly Gly Glu Ala Ala Arg Gly Pro Glu
            355                 360                 365

<210> SEQ ID NO 3
<211> LENGTH: 1107
<212> TYPE: DNA
<213> ORGANISM: human

<400> SEQUENCE: 3
atggctgatg cccagaacat ttcactggac agcccaggga gtgtgggggc cgtggcagtg      60
cctgtggtct ttgccctaat cttcctgctg gcacagtgg gcaatgggct ggtgctggca     120
gtgctcctgc agcctggccc gagtgcctgg caggagcctg cagcaccac ggacctgttc     180 atcctcaacc tggcggtggc tgacctctgc ttcatcctgt gctgcgtgcc cttccaggcc     240
accatctaca cgctggatgc ctggctcttt ggggccctcg tctgcaaggc cgtgcacctg     300
ctcatctacc tcaccatgta cgccagcagc tttacgctgg ctgctgtctc cgtggacagg     360
tacctggccg tgcggcaccc gctgcgctcg cgcccctgc gcacgccgcg taacgcccgc     420
gccgcagtgg ggctggtgtg gctgctggcg gcgctcttct cggcgcccta cctcagctac     480
tacggcaccg tgcgctacgg cgcgctggag ctctgcgtgc cgcctgggga ggacgcgcgc     540
cgccgcgccc tggacgtggc caccttcgct gccggctacc tgctgcccgt ggctgtggtg     600
agcctggcct acgggcgcac gctgcgcttc tgtgggccg ccgtgggtcc cgcgggcgcg     660
gcggcggccg aggcgcggcg gagggcgacg ggccgcgcgg ggcgcgccat gctggcggtg     720
gccgcgctct acgcgctctg ctgggtccg caccacgcgc tcatcctgtg cttctggtac     780
ggccgcttcg ccttcagccc ggccacctac gcctgccgcc tggcctcaca ctgcctggcc     840
tacgccaact cctgcctcaa cccgctcgtc tacgcgctcg cctcgcgcca cttccgcgcg     900
```

-continued

```
cgcttccgcc gcctgtggcc gtgcggccgc cgacgccgcc accgtgcccg ccgcgccttg      960
cgtcgcgtcc gccccgcgtc ctcgggccca cccggctgcc ccggagacgc ccggcctagc     1020
gggaggctgc tggctggtgg cggccagggc ccggagccca gggagggacc cgtccacggc     1080
ggagaggctg cccgaggacc ggaataa                                          1107
```

<210> SEQ ID NO 4
<211> LENGTH: 368
<212> TYPE: PRT
<213> ORGANISM: human

<400> SEQUENCE: 4

```
Met Ala Asp Ala Gln Asn Ile Ser Leu Asp Ser Pro Gly Ser Val Gly
 1               5                  10                  15

Ala Val Ala Val Pro Val Val Phe Ala Leu Ile Phe Leu Leu Gly Thr
            20                  25                  30

Val Gly Asn Gly Leu Val Leu Ala Val Leu Leu Gln Pro Gly Pro Ser
        35                  40                  45

Ala Trp Gln Glu Pro Gly Ser Thr Thr Asp Leu Phe Ile Leu Asn Leu
    50                  55                  60

Ala Val Ala Asp Leu Cys Phe Ile Leu Cys Cys Val Pro Phe Gln Ala
65                  70                  75                  80

Thr Ile Tyr Thr Leu Asp Ala Trp Leu Phe Gly Ala Leu Val Cys Lys
                85                  90                  95

Ala Val His Leu Leu Ile Tyr Leu Thr Met Tyr Ala Ser Ser Phe Thr
            100                 105                 110

Leu Ala Ala Val Ser Val Asp Arg Tyr Leu Ala Val Arg His Pro Leu
        115                 120                 125

Arg Ser Arg Ala Leu Arg Thr Pro Arg Asn Ala Arg Ala Ala Val Gly
    130                 135                 140

Leu Val Trp Leu Leu Ala Ala Leu Phe Ser Ala Pro Tyr Leu Ser Tyr
145                 150                 155                 160

Tyr Gly Thr Val Arg Tyr Gly Ala Leu Glu Leu Cys Val Pro Ala Trp
                165                 170                 175

Glu Asp Ala Arg Arg Arg Ala Leu Asp Val Ala Thr Phe Ala Ala Gly
            180                 185                 190

Tyr Leu Leu Pro Val Ala Val Ser Leu Ala Tyr Gly Arg Thr Leu
        195                 200                 205

Arg Phe Leu Trp Ala Ala Val Gly Pro Ala Gly Ala Ala Ala Ala Glu
    210                 215                 220

Ala Arg Arg Arg Ala Thr Gly Arg Ala Gly Arg Ala Met Leu Ala Val
225                 230                 235                 240

Ala Ala Leu Tyr Ala Leu Cys Trp Gly Pro His His Ala Leu Ile Leu
                245                 250                 255

Cys Phe Trp Tyr Gly Arg Phe Ala Phe Ser Pro Ala Thr Tyr Ala Cys
            260                 265                 270

Arg Leu Ala Ser His Cys Leu Ala Tyr Ala Asn Ser Cys Leu Asn Pro
        275                 280                 285

Leu Val Tyr Ala Leu Ala Ser Arg His Phe Arg Ala Arg Phe Arg Arg
    290                 295                 300

Leu Trp Pro Cys Gly Arg Arg Arg His Ala Arg Arg Ala Leu
305                 310                 315                 320

Arg Arg Val Arg Pro Ala Ser Ser Gly Pro Pro Gly Cys Pro Gly Asp
                325                 330                 335
```

```
Ala Arg Pro Ser Gly Arg Leu Leu Ala Gly Gly Gln Gly Pro Glu
            340                 345                 350

Pro Arg Glu Gly Pro Val His Gly Gly Glu Ala Ala Arg Gly Pro Glu
            355                 360                 365

<210> SEQ ID NO 5
<211> LENGTH: 348
<212> TYPE: PRT
<213> ORGANISM: mouse

<400> SEQUENCE: 5

Met Glu Leu Ala Met Val Asn Leu Ser Glu Gly Asn Gly Ser Asp Pro
  1               5                  10                  15

Glu Pro Pro Ala Pro Glu Ser Arg Pro Leu Phe Gly Ile Gly Val Glu
                 20                  25                  30

Asn Phe Ile Thr Leu Val Val Phe Gly Leu Ile Phe Ala Met Gly Val
             35                  40                  45

Leu Gly Asn Ser Leu Val Ile Thr Val Leu Ala Arg Ser Lys Pro Gly
         50                  55                  60

Lys Pro Arg Ser Thr Thr Asn Leu Phe Ile Leu Asn Leu Ser Ile Ala
 65                  70                  75                  80

Asp Leu Ala Tyr Leu Leu Phe Cys Ile Pro Phe Gln Ala Thr Val Tyr
                 85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
            115                 120                 125

Met Ser Val Asp Arg Tyr Val Ala Ile Val His Ser Arg Arg Ser Ser
        130                 135                 140

Ser Leu Arg Val Ser Arg Asn Ala Leu Leu Gly Val Gly Phe Ile Trp
145                 150                 155                 160

Ala Leu Ser Ile Ala Met Ala Ser Pro Val Ala Tyr His Gln Arg Leu
                165                 170                 175

Phe His Arg Asp Ser Asn Gln Thr Phe Cys Trp Glu Gln Trp Pro Asn
            180                 185                 190

Lys Leu His Lys Lys Ala Tyr Val Val Cys Thr Phe Val Phe Gly Tyr
        195                 200                 205

Leu Leu Pro Leu Leu Leu Ile Cys Phe Cys Tyr Ala Lys Val Leu Asn
    210                 215                 220

His Leu His Lys Lys Leu Lys Asn Met Ser Lys Lys Ser Glu Ala Ser
225                 230                 235                 240

Lys Lys Lys Thr Ala Gln Thr Val Leu Val Val Val Val Val Phe Gly
                245                 250                 255

Ile Ser Trp Leu Pro His His Val His Leu Trp Ala Glu Phe Gly
            260                 265                 270

Ala Phe Pro Leu Thr Pro Ala Ser Phe Phe Arg Ile Thr Ala His
        275                 280                 285

Cys Leu Ala Tyr Ser Asn Ser Ser Val Asn Pro Ile Ile Tyr Ala Phe
    290                 295                 300

Leu Ser Glu Asn Phe Arg Lys Ala Tyr Lys Gln Val Phe Lys Cys His
305                 310                 315                 320

Val Cys Asp Glu Ser Pro Arg Ser Glu Thr Lys Glu Asn Lys Ser Arg
                325                 330                 335

Met Asp Thr Pro Pro Ser Thr Asn Cys Thr His Val
```

<210> SEQ ID NO 6
<211> LENGTH: 346
<212> TYPE: PRT
<213> ORGANISM: rat

<400> SEQUENCE: 6

Met Glu Leu Ala Pro Val Asn Leu Ser Glu Gly Asn Gly Ser Asp Pro
1               5                   10                  15

Glu Pro Pro Ala Glu Pro Arg Pro Leu Phe Gly Ile Gly Val Glu Asn
            20                  25                  30

Phe Ile Thr Leu Val Val Phe Gly Leu Ile Phe Ala Met Gly Val Leu
        35                  40                  45

Gly Asn Ser Leu Val Ile Thr Val Leu Ala Arg Ser Lys Pro Gly Lys
    50                  55                  60

Pro Arg Ser Thr Thr Asn Leu Phe Ile Leu Asn Leu Ser Ile Ala Asp
65                  70                  75                  80

Leu Ala Tyr Leu Leu Phe Cys Ile Pro Phe Gln Ala Thr Val Tyr Ala
                85                  90                  95

Leu Pro Thr Trp Val Leu Gly Ala Phe Ile Cys Lys Phe Ile His Tyr
            100                 105                 110

Phe Phe Thr Val Ser Met Leu Val Ser Ile Phe Thr Leu Ala Ala Met
        115                 120                 125

Ser Val Asp Arg Tyr Val Ala Ile Val His Ser Arg Arg Ser Ser Ser
    130                 135                 140

Leu Arg Val Ser Arg Asn Ala Leu Leu Gly Val Gly Phe Ile Trp Ala
145                 150                 155                 160

Leu Ser Ile Ala Met Ala Ser Pro Val Ala Tyr Tyr Gln Arg Leu Phe
                165                 170                 175

His Arg Asp Ser Asn Gln Thr Phe Cys Trp Glu His Trp Pro Asn Gln
            180                 185                 190

Leu His Lys Lys Ala Tyr Val Val Cys Thr Phe Val Phe Gly Tyr Leu
        195                 200                 205

Leu Pro Leu Leu Leu Ile Cys Phe Cys Tyr Ala Lys Val Leu Asn His
    210                 215                 220

Leu His Lys Lys Leu Lys Asn Met Ser Lys Lys Ser Glu Ala Ser Lys
225                 230                 235                 240

Lys Lys Thr Ala Gln Thr Val Leu Val Val Val Val Phe Gly Ile
                245                 250                 255

Ser Trp Leu Pro His His Val Ile His Leu Trp Ala Glu Phe Gly Ala
            260                 265                 270

Phe Pro Leu Thr Pro Ala Ser Phe Phe Arg Ile Thr Ala His Cys
        275                 280                 285

Leu Ala Tyr Ser Asn Ser Ser Val Asn Pro Ile Ile Tyr Ala Phe Leu
    290                 295                 300

Ser Glu Asn Phe Arg Lys Ala Tyr Lys Gln Val Phe Lys Cys Arg Val
305                 310                 315                 320

Cys Asn Glu Ser Pro His Gly Asp Ala Lys Glu Lys Asn Arg Ile Asp
                325                 330                 335

Thr Pro Pro Ser Thr Asn Cys Thr His Val
            340                 345

<210> SEQ ID NO 7
<211> LENGTH: 349

<212> TYPE: PRT
<213> ORGANISM: human

<400> SEQUENCE: 7

```
Met Glu Leu Ala Val Gly Asn Leu Ser Glu Gly Asn Ala Ser Cys Pro
 1               5                  10                  15
Glu Pro Pro Ala Pro Glu Pro Gly Pro Leu Phe Gly Ile Gly Val Glu
                20                  25                  30
Asn Phe Val Thr Leu Val Val Phe Gly Leu Ile Phe Ala Leu Gly Val
                35                  40                  45
Leu Gly Asn Ser Leu Val Ile Thr Val Leu Ala Arg Ser Lys Pro Gly
            50                  55                  60
Lys Pro Arg Ser Thr Thr Asn Leu Phe Ile Leu Asn Leu Ser Ile Ala
 65                 70                  75                  80
Asp Leu Ala Tyr Leu Leu Phe Cys Ile Pro Phe Gln Ala Thr Val Tyr
                85                  90                  95
Ala Leu Pro Thr Trp Val Leu Gly Ala Phe Ile Cys Lys Phe Ile His
                100                 105                 110
Tyr Phe Phe Thr Val Ser Met Leu Val Ser Ile Phe Thr Leu Ala Ala
                115                 120                 125
Met Ser Val Asp Arg Tyr Val Ala Ile Val His Ser Arg Arg Ser Ser
 130                135                 140
Ser Leu Arg Val Ser Arg Asn Ala Leu Leu Gly Val Gly Cys Ile Trp
 145                150                 155                 160
Ala Leu Ser Ile Ala Met Ala Ser Pro Val Ala Tyr His Gln Gly Leu
                165                 170                 175
Phe His Pro Arg Ala Ser Asn Gln Thr Phe Cys Trp Glu Gln Trp Pro
                180                 185                 190
Asp Pro Arg His His Lys Lys Ala Tyr Val Val Cys Thr Phe Val Phe Gly
                195                 200                 205
Tyr Leu Leu Pro Leu Leu Ile Cys Phe Cys Tyr Ala Lys Val Leu
                210                 215                 220
Asn His Leu His Lys Lys Leu Lys Asn Met Ser Lys Lys Ser Glu Ala
 225                230                 235                 240
Ser Lys Lys Lys Thr Ala Gln Thr Val Leu Val Val Val Val Val Phe
                245                 250                 255
Gly Ile Ser Trp Leu Pro His His Ile Ile His Leu Trp Ala Glu Phe
                260                 265                 270
Gly Val Phe Pro Leu Thr Pro Ala Ser Phe Leu Phe Arg Ile Thr Ala
                275                 280                 285
His Cys Leu Ala Tyr Ser Asn Ser Ser Val Asn Pro Ile Ile Tyr Ala
                290                 295                 300
Phe Leu Ser Glu Asn Phe Arg Lys Ala Tyr Lys Gln Val Phe Lys Cys
 305                310                 315                 320
His Ile Arg Lys Asp Ser His Leu Ser Asp Thr Lys Glu Asn Lys Ser
                325                 330                 335
Arg Ile Asp Thr Pro Pro Ser Thr Asn Cys Thr His Val
                340                 345
```

<210> SEQ ID NO 8
<211> LENGTH: 371
<212> TYPE: PRT
<213> ORGANISM: mouse

<400> SEQUENCE: 8

```
Met Asn Gly Ser Asp Ser Gln Gly Ala Glu Asp Ser Ser Gln Glu Gly
 1               5                  10                  15

Gly Gly Gly Trp Gln Pro Glu Ala Val Leu Val Pro Leu Phe Phe Ala
            20                  25                  30

Leu Ile Phe Leu Val Gly Ala Val Gly Asn Ala Leu Val Leu Ala Val
        35                  40                  45

Leu Leu Arg Gly Gly Gln Ala Val Ser Thr Thr Asn Leu Phe Ile Leu
50                  55                  60

Asn Leu Gly Val Ala Asp Leu Cys Phe Ile Leu Cys Cys Val Pro Phe
65                  70                  75                  80

Gln Ala Thr Ile Tyr Thr Leu Asp Asp Trp Val Phe Gly Ser Leu Leu
                85                  90                  95

Cys Lys Ala Val His Phe Leu Ile Phe Leu Thr Met His Ala Ser Ser
                100                 105                 110

Phe Thr Leu Ala Ala Val Ser Leu Asp Arg Tyr Leu Ala Ile Arg Tyr
            115                 120                 125

Pro Met His Ser Arg Glu Leu Arg Thr Pro Arg Asn Ala Leu Ala Ala
        130                 135                 140

Ile Gly Leu Ile Trp Gly Leu Ala Leu Leu Phe Ser Gly Pro Tyr Leu
145                 150                 155                 160

Ser Tyr Tyr Ser Gln Ser Gln Leu Ala Asn Leu Thr Val Cys His Pro
                165                 170                 175

Ala Trp Ser Ala Pro Arg Arg Arg Ala Met Asp Leu Cys Thr Phe Val
            180                 185                 190

Phe Ser Tyr Leu Leu Pro Val Leu Val Leu Ser Leu Thr Tyr Ala Arg
        195                 200                 205

Thr Leu His Tyr Leu Trp Arg Thr Val Asp Pro Val Ala Ala Gly Ser
        210                 215                 220

Gly Ser Gln Arg Ala Lys Arg Lys Val Thr Arg Met Ile Val Ile Val
225                 230                 235                 240

Ala Val Leu Phe Cys Leu Cys Trp Met Pro His His Ala Leu Ile Leu
                245                 250                 255

Cys Val Trp Phe Gly Arg Phe Pro Leu Thr Arg Ala Thr Tyr Ala Leu
            260                 265                 270

Arg Ile Leu Ser His Leu Val Ser Tyr Ala Asn Ser Cys Val Asn Pro
        275                 280                 285

Ile Val Tyr Ala Leu Val Ser Lys His Phe Arg Lys Gly Phe Arg Lys
290                 295                 300

Ile Cys Ala Gly Leu Leu Arg Arg Ala Pro Arg Arg Ala Ser Gly Arg
305                 310                 315                 320

Val Cys Ile Leu Ala Pro Gly Asn His Ser Gly Met Leu Glu Pro
                325                 330                 335

Glu Ser Thr Asp Leu Thr Gln Val Ser Glu Ala Ala Gly Pro Leu Val
            340                 345                 350

Pro Ala Pro Ala Leu Pro Asn Cys Thr Thr Leu Ser Arg Thr Leu Asp
        355                 360                 365

Pro Ala Cys
        370

<210> SEQ ID NO 9
<211> LENGTH: 372
<212> TYPE: PRT
<213> ORGANISM: rat

<400> SEQUENCE: 9
```

-continued

```
Met Asn Gly Ser Gly Ser Gln Gly Ala Glu Asn Thr Ser Gln Glu Gly
 1               5                  10                  15

Gly Ser Gly Gly Trp Gln Pro Glu Ala Val Leu Val Pro Leu Phe Phe
            20                  25                  30

Ala Leu Ile Phe Leu Val Gly Thr Val Gly Asn Ala Leu Val Leu Ala
            35                  40                  45

Val Leu Leu Arg Gly Gly Gln Ala Val Ser Thr Thr Asn Leu Phe Ile
        50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Asp Trp Val Phe Gly Ser Leu
                85                  90                  95

Leu Cys Lys Ala Val His Phe Leu Ile Phe Leu Thr Met His Ala Ser
                100                 105                 110

Ser Phe Thr Leu Ala Ala Val Ser Leu Asp Arg Tyr Leu Ala Ile Arg
            115                 120                 125

Tyr Pro Leu His Ser Arg Glu Leu Arg Thr Pro Arg Asn Ala Leu Ala
        130                 135                 140

Ala Ile Gly Leu Ile Trp Gly Leu Ala Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Arg Ala Met Asp Leu Cys Thr Phe
            180                 185                 190

Val Phe Ser Tyr Leu Leu Pro Val Leu Val Leu Ser Leu Thr Tyr Ala
        195                 200                 205

Arg Thr Leu Arg Tyr Leu Trp Arg Thr Val Asp Pro Val Thr Ala Gly
    210                 215                 220

Ser Gly Ser Gln Arg Ala Lys Arg Lys Val Thr Arg Met Ile Ile Ile
225                 230                 235                 240

Val Ala Val Leu Phe Cys Leu Cys Trp Met Pro His His Ala Leu Ile
                245                 250                 255

Leu Cys Val Trp Phe Gly Arg Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300

Lys Ile Cys Ala Gly Leu Leu Arg Pro Ala Pro Arg Arg Ala Ser Gly
305                 310                 315                 320

Arg Val Ser Ile Leu Ala Pro Gly Asn His Ser Gly Ser Met Leu Glu
                325                 330                 335

Gln Glu Ser Thr Asp Leu Thr Gln Val Ser Glu Ala Ala Gly Pro Leu
            340                 345                 350

Val Pro Pro Pro Ala Leu Pro Asn Cys Thr Ala Ser Ser Arg Thr Leu
        355                 360                 365

Asp Pro Ala Cys
    370
```

<210> SEQ ID NO 10
<211> LENGTH: 387
<212> TYPE: PRT
<213> ORGANISM: human

<400> SEQUENCE: 10

```
Met Asn Val Ser Gly Cys Pro Gly Ala Gly Asn Ala Ser Gln Ala Gly
1               5                   10                  15

Gly Gly Gly Gly Trp His Pro Glu Ala Val Ile Val Pro Leu Leu Phe
            20                  25                  30

Ala Leu Ile Phe Leu Val Gly Thr Val Gly Asn Thr Leu Val Leu Ala
        35                  40                  45

Val Leu Leu Arg Gly Gly Gln Ala Val Ser Thr Thr Asn Leu Phe Ile
50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Gly Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ser Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Ala Met Asp Ile Cys Thr Phe
            180                 185                 190

Val Phe Ser Tyr Leu Leu Pro Val Leu Val Leu Gly Leu Thr Tyr Ala
        195                 200                 205

Arg Thr Leu Arg Tyr Leu Trp Arg Ala Val Asp Pro Val Ala Ala Gly
    210                 215                 220

Ser Gly Ala Arg Arg Ala Lys Arg Lys Val Thr Arg Met Ile Leu Ile
225                 230                 235                 240

Val Ala Ala Leu Phe Cys Leu Cys Trp Met Pro His His Ala Leu Ile
                245                 250                 255

Leu Cys Val Trp Phe Gly Gln Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300

Thr Ile Cys Ala Gly Leu Leu Gly Arg Ala Pro Gly Arg Ala Ser Gly
305                 310                 315                 320

Arg Val Cys Ala Ala Arg Gly Thr His Ser Gly Ser Val Leu Glu
                325                 330                 335

Arg Glu Ser Ser Asp Leu Leu His Met Ser Glu Ala Ala Gly Ala Leu
            340                 345                 350

Arg Pro Cys Pro Gly Ala Ser Gln Pro Cys Ile Leu Glu Pro Cys Pro
        355                 360                 365

Gly Pro Ser Trp Gln Gly Pro Lys Ala Gly Asp Ser Ile Leu Thr Val
    370                 375                 380

Asp Val Ala
385
```

<210> SEQ ID NO 11

```
<211> LENGTH: 390
<212> TYPE: DNA
<213> ORGANISM: rat

<400> SEQUENCE: 11
ccctacctca gctactacgg cacggtgcgc tacggccggc tcgagctctg cgtgcccgct      60
tgggaggagg acgcgcggcg gcgcgcgctg gacgtggcca ccttcgccgc gggctacctg     120
ctgccggtgg ccgtggtgag cctggcctac ggacgcacgc tatgtttcct atgggccgcc    180
gtgggtcccg cgggcagcgc ggcagcagag gcgcgcagag gggcgaccgg ccgggcggga    240
cgccgcatgc tggcagtggc gctctacgcg ctttgctggg gcccgcacca cgcgctcatc    300
ctctgcttct ggtacggtcc gttcgccttc agcccggcca cctacgcctg tcgcctggcc    360
tcacactgcc tcgcctacgc caactcctgc                                     390

<210> SEQ ID NO 12
<211> LENGTH: 129
<212> TYPE: PRT
<213> ORGANISM: rat

<400> SEQUENCE: 12

Pro Tyr Leu Ser Tyr Tyr Gly Thr Val Arg Tyr Gly Arg Leu Glu Leu
  1               5                  10                  15

Cys Val Pro Ala Trp Glu Asp Ala Arg Arg Ala Leu Asp Val Ala
                 20                  25                  30

Thr Phe Ala Ala Gly Tyr Leu Leu Pro Val Ala Val Ser Leu Ala
             35                  40                  45

Tyr Gly Arg Thr Leu Cys Phe Leu Trp Ala Ala Val Gly Pro Ala Gly
     50                  55                  60

Ser Ala Ala Glu Ala Arg Arg Ala Thr Gly Arg Ala Gly Arg
 65                  70                  75                  80

Arg Met Leu Ala Val Ala Leu Tyr Ala Leu Cys Trp Gly Pro His His
                 85                  90                  95

Ala Leu Ile Leu Cys Phe Trp Tyr Gly Pro Phe Ala Phe Ser Pro Ala
                100                 105                 110

Thr Tyr Ala Cys Arg Leu Ala Ser His Cys Leu Ala Tyr Ala Asn Ser
            115                 120                 125

Cys

<210> SEQ ID NO 13
<211> LENGTH: 34
<212> TYPE: DNA
<213> ORGANISM: Artificial Sequence
<220> FEATURE:
<223> OTHER INFORMATION: PCR primer

<400> SEQUENCE: 13
gcgaattcgg taccatggct gatgcccaga acat                                 34

<210> SEQ ID NO 14
<211> LENGTH: 23
<212> TYPE: DNA
<213> ORGANISM: Artificial Sequence
<220> FEATURE:
<223> OTHER INFORMATION: PCR primer

<400> SEQUENCE: 14
cgcctgtcga cagatacagc agc                                             23
```

```
<210> SEQ ID NO 15
<211> LENGTH: 37
<212> TYPE: DNA
<213> ORGANISM: Artificial Sequence
<220> FEATURE:
<223> OTHER INFORMATION: PCR primer

<400> SEQUENCE: 15
tgtatctgtc gacaggtaac ctggccgtgc ggcaccc                              37

<210> SEQ ID NO 16
<211> LENGTH: 28
<212> TYPE: DNA
<213> ORGANISM: Artificial Sequence
<220> FEATURE:
<223> OTHER INFORMATION: PCR primer

<400> SEQUENCE: 16
gcgcggccgc ttattccggt cctcgggc                                        28
```